United States Patent [19]
Buchwald

[11] Patent Number: 5,290,439
[45] Date of Patent: Mar. 1, 1994

[54] DEVICE FOR PURIFYING A FLOW OF LIQUID BY MEANS OF ULTRAVIOLET RADIATION

[76] Inventor: Claus Buchwald, 6596 de la Riviére, Val Morin, (Québec) J0T 2R0, Canada

[21] Appl. No.: 897,392

[22] Filed: Jun. 12, 1992

[51] Int. Cl.⁵ ............................................. C02F 1/32
[52] U.S. Cl. ................... 210/198.1; 210/748; 210/252; 210/253; 422/186.3; 250/436
[58] Field of Search ............ 210/748, 198.1, 192, 210/252, 253; 422/24, 186.3; 250/435, 436, 437, 438

[56] References Cited

U.S. PATENT DOCUMENTS

| | | | |
|---|---|---|---|
| 3,462,597 | 8/1969 | Young | 250/436 |
| 3,471,693 | 10/1969 | Veloz | 250/436 |
| 4,141,686 | 2/1979 | Lewis | 250/436 |
| 4,535,247 | 8/1985 | Kurtz | 250/436 |
| 4,963,750 | 10/1990 | Wilson | 250/436 |
| 4,968,489 | 11/1990 | Peterson | 250/436 |
| 5,166,527 | 11/1992 | Solymar | 250/436 |

Primary Examiner—Neil M. McCarthy
Attorney, Agent, or Firm—Michael D. Bednarek

[57] ABSTRACT

The device for purifying a flow of liquid by means of ultraviolet radiation, includes an elongated ultraviolet lamp; a generally tubular inner casing surrounding substantially the lamp, the casing being made of a material that allows transmission of ultraviolet radiation, the casing having an aperture at each end thereof from which the electrical terminals of the lamp protrude; and a generally tubular outer casing surrounding the inner casing and forming with it a flow passage, the outer casing being provided at substantially each of its ends with inlet and outlet for the flow of liquid. Two connectors are disposed respectively at both ends of the device for securing the lamp and the inner casing with respect to the outer casing. Each connector includes an annular liquid-tight removable seal disposed between inner and outer casings; an opaque electrical socket having a central cavity for receiving the corresponding terminal of the lamp; and a fixing device for securing the corresponding socket and seal with respect to said casings and lamp.

6 Claims, 6 Drawing Sheets

DEVICE FOR PURIFYING A FLOW OF LIQUID BY MEANS OF ULTRAVIOLET RADIATION

BACKGROUND OF THE INVENTION

The present invention relates to a device for purifying a flow of liquid by means of ultraviolet radiation.

Known in the art, there is the German Patent No. 3,117,473, showing a device for purifying water by means of ultraviolet radiation. One of the drawbacks with this device is that the ultraviolet lamp is directly exposed to ambient atmosphere so that when the device is operating, ultraviolet rays are emitted at each end of the device. This can be dangerous for children looking directly at the ultraviolet lamp.

Also, when the user wants to replace the lamp, the removing of the lamp cannot be done in a simple operation.

Also known in the art, there is the U.S. Pat. No. 4,752,401, granted on Jun. 21, 1988, and assigned to the company Safe Water Systems International. This patent describes a water treatment system for swimming pools and potable water.

One problem with this system is that when the ultraviolet lamp has to be replaced, this cannot be done in a simple operation. Also, the ultraviolet lamp is directly in contact with the water flow, which is hazardous.

Also known in the art, there are the following patents:

| Canadian Patent No.: | | |
|---|---|---|
| 1,054,331 | Douglas LAMBERT et al | 1979 |
| German Patent Nos.: | | |
| 1,545,595 | | |
| 3,624,169 | | |
| U.S. Pat. No.: | | |
| 5,026,477 | J-C YEN | 1991. |

None of the above-mentioned patents can provide a safe device that does not emit ultraviolet rays in the ambient atmosphere and a device that can provide the necessary means for easily replacing the ultraviolet lamp when it is needed.

It is an object of the present invention to provide a device for purifying a flow of liquid by means of ultraviolet radiation that is safe to operate, and that provides means by which the ultraviolet lamp can easily be replaced when it is needed.

SUMMARY OF THE INVENTION

According to the present invention, there is provided a device for purifying a flow of liquid by means of ultraviolet radiation, comprising:

an elongated ultraviolet lamp having electrical terminals at each end thereof;

a generally tubular inner casing surrounding substantially said lamp, said casing being made of a material that allow transmission of ultraviolet radiation, said casing having an aperture at each end thereof from which said electrical terminals protrude;

a generally tubular outer casing surrounding said inner casing and forming with said inner casing a flow passage of generally annular cross-section for accommodating said flow of liquid, said outer casing being provided at substantially each of its ends with inlet and outlet for said flow of liquid, said outer casing being made of opaque material;

two connectors disposed respectively at both ends of said device for securing said lamp and said inner casing with respect to said outer casing, each of said connectors comprising.

an annular liquid-tight removable seal disposed between said inner and outer casings;

an opaque electrical socket having a central cavity for receiving the corresponding terminal of the lamp; and a fixing means for securing the corresponding socket and seal with respect to said casings and lamp; said casings, said seals and said sockets being made of material resistant to degradation by ultraviolet radiation;

whereby people surrounding said device when it is operating are never exposed to ultraviolet radiation, and whereby a user can have an easy access to said lamp by removing said fixing means.

The object, advantages and other features of the present invention will become more apparent upon reading of the following non-restrictive description of a preferred embodiment thereof, given for the purpose of exemplification only with reference to the accompanying drawings.

DETAILED DESCRIPTION OF THE DRAWINGS

Figure 1:
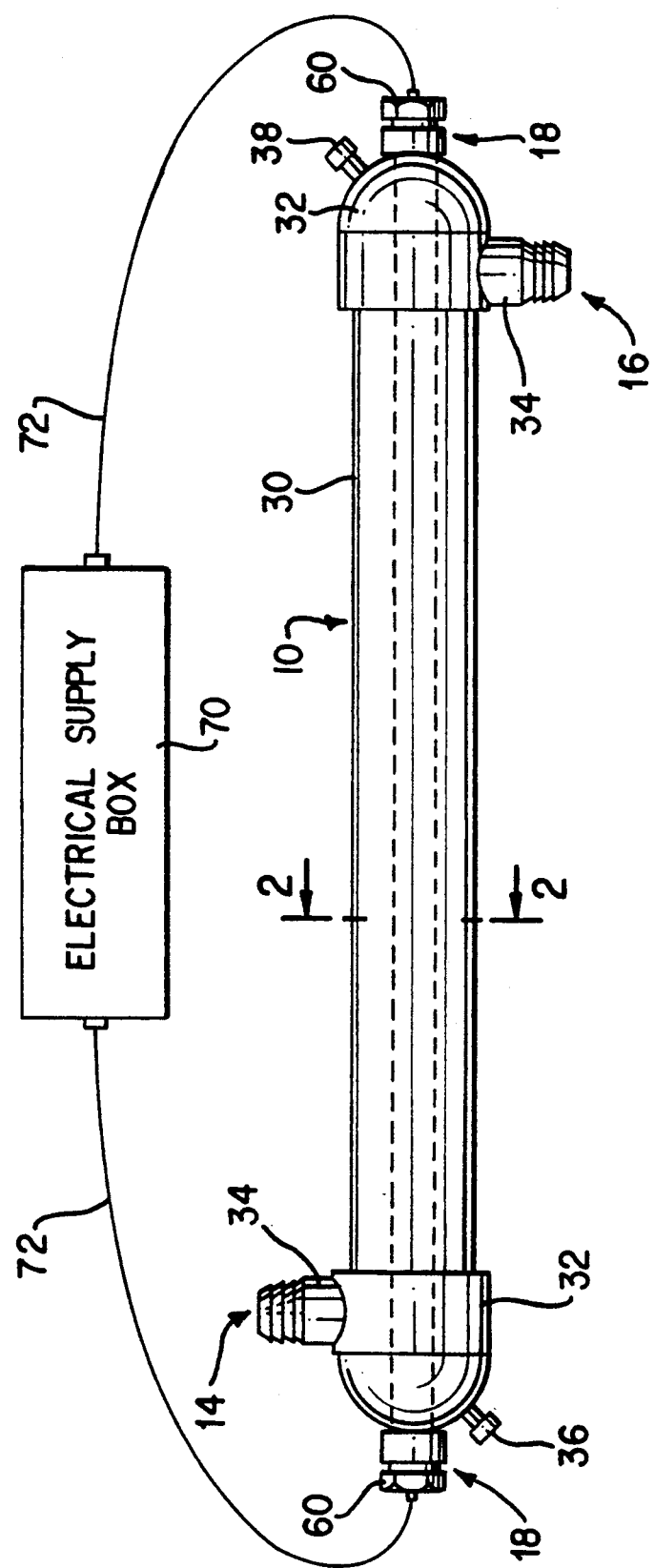
FIG. 1 is a side view of a first embodiment of the present invention, that is connected to an electrical supply box.
Figure 5:
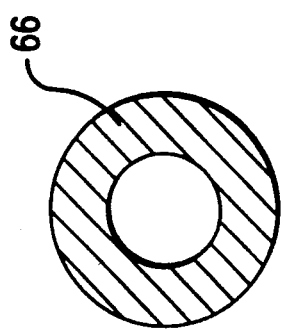
FIG. 5 is a side view along line 5—5 of FIG. 3.
Figure 7:
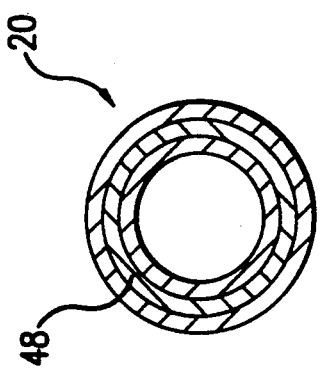
FIG. 7 is a side view along line 7—7 of FIG. 3.
Figure 4:
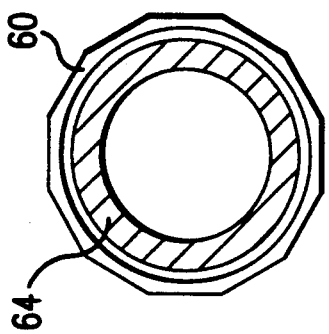
FIG. 4 is a side view along line 4—4 of FIG. 3.
Figure 6:
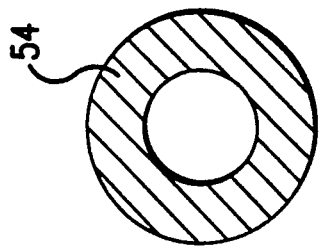
FIG. 6 is a side view along line 6—6 of FIG. 3.

Referring now to FIGS. 1, 2, 3, 4, 5, 6 and 7, there is shown a device for purifying a flow of liquid by means of ultraviolet radiation. The device comprises an elongated ultraviolet lamp 2 having electrical terminals 4 at each end thereof. A generally tubular inner casing 6 is provided. It surrounds substantially the lamp 2. The casing 6 is made of a material that allows transmission of ultraviolet radiation. The casing 6 has an aperture 8 at each end thereof from which the electrical terminals 4 protrude.

A generally tubular outer casing 10 is provided. It surrounds the inner casing 6 and forms with it a flow passage 12 of generally annular cross-section for accommodating the flow of liquid. The outer casing 10 is provided at substantially each of its ends with inlet 14 and outlet 16 for the flow of liquid. The outer casing is made of opaque material that does not allow transmission of ultraviolet radiation.

Two connectors 18 are disposed respectively at both ends of the device for securing the lamp 2 and the inner casing 6 with respect to the outer casing 10. Each of the connectors 18 comprises an annular liquid-tight removable seal 20 disposed between the inner and outer casings 6 and 10; an opaque electrical socket 22 having a central cavity for receiving the corresponding terminal 4 of the lamp 2; and a fixing device for securing the corresponding socket 22 and seal 20 with respect to the casings 6, 10 and lamp 2. The casings 6 and 10, the seals 20 and the sockets 22 are made of a material resistant to degradation by ultraviolet radiation. With the above described device, as ultraviolet lamp 2 is completely surrounded by material that does not allow transmission of ultraviolet radiation, people can surround the device when it is operating and are never exposed to ultraviolet radiation. Also, a user can have an easy access to the lamp 2 by removing the fixing device.

The outer casing 10 comprises an elongated tubular central portion 30; and two end portions 32 disposed respectively at both sides of the central portion 30. Each of the end portions 32 has a first aperture for receiving the corresponding end of the central portion 30. Each of the end portions 32 is provided with a lateral aperture receiving a male barbed hose fitting 34 forming the inlet 14 or outlet 16. One of the end portions 32 is provided with a drain valve 38. The other end portion 32 is provided with a breather valve 36. Each of the end portions 32 is provided with a second aperture opposite to the first aperture to receive the corresponding connector 18. The second aperture is provided on its inner portion with threads 40 and with a bevelled edge 42 for receiving the corresponding annular seal 20.

The inner casing 30 has each of its ends provided with a bevelled edge 46 for receiving the corresponding annular seal 20. Each of the seals 20 has an end provided with a protruding portion 48 cooperating with the corresponding bevelled edges 46 and 42 of inner and outer casings 6 and 10, and an opposite end provided with a stop 50.

Each of the fixing device comprises a first tubular element 52 having threads on its outer surface to be engaged with the threads 40 of the end portion of the outer casing 10. An annular metal washer 54 is provided. It has one side to be disposed against the stop 50 of the seal 20 and another side to receive an edge of the tubular element 52 when it is screwed with the end portion of the outer casing 10 to hold the seal 50 in liquid-tight position between inner and outer casings 6 and 10.

A second tubular element 60 is provided. It has threads on its inner surface 62, to be engaged with the threads of the tubular element 52. The second element 60 is provided with a stop 64 at its outer end to rest against the first tubular element 52 and socket 22 when it is screwed upon the first tubular element 52.

An annular rubber washer 66 is disposed between the stop 64 and the first tubular element 52 and socket 22.

Referring now most specifically to FIG. 1, there is shown an electrical supply box 70 having electrical wires 72 connected respectively to the terminals of the lamp to energize it. This electrical box 70 contains all the electrical components necessary for the proper functioning of the ultraviolet generating lamp such as ballast, relays, fuses, warning lights, etc. As the combination of the above-mentioned elements is very well-known in the art, the elements of the electrical supply box are not illustrated in detail.

Figure 8:
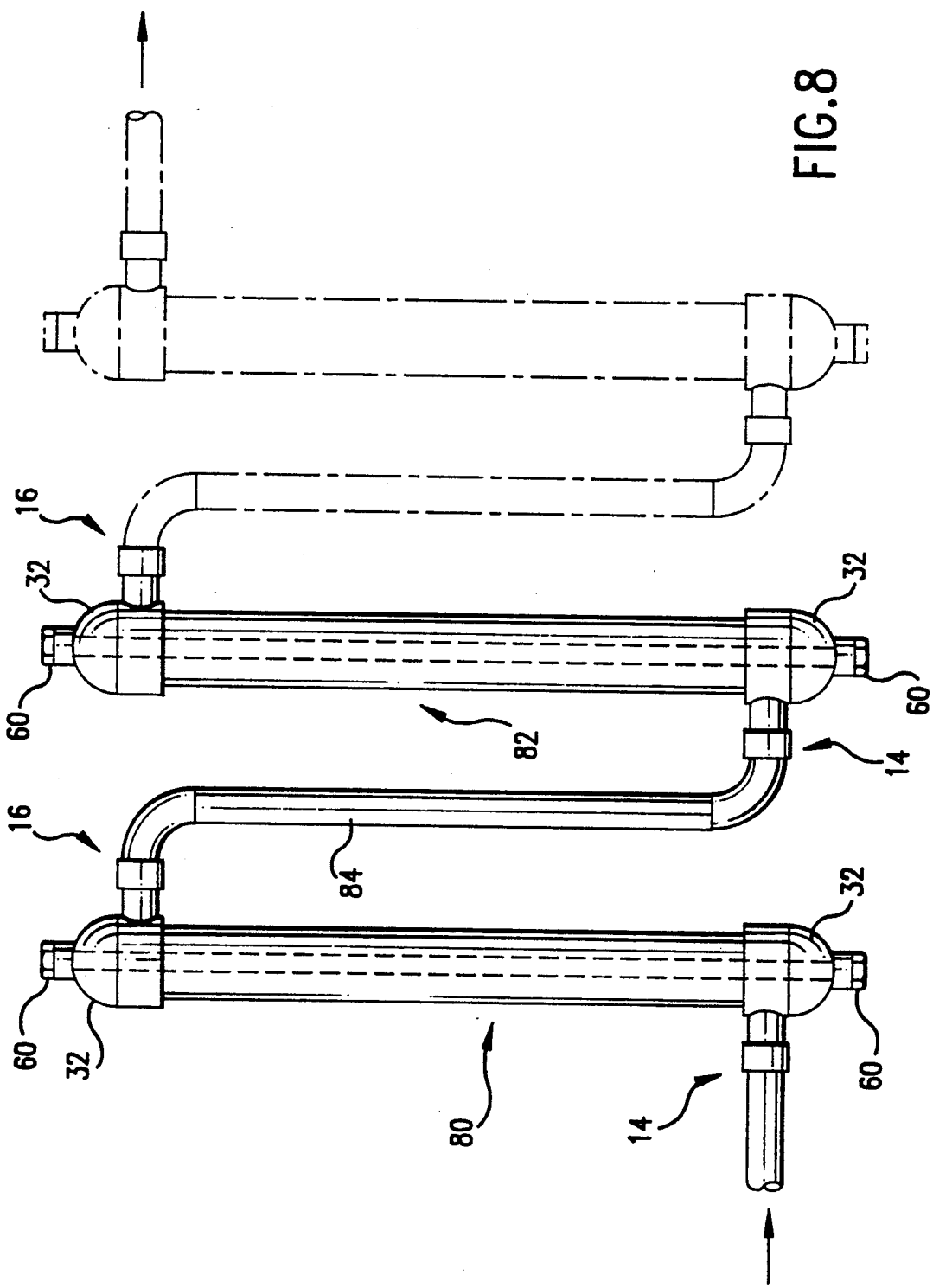
FIG. 8 is a side view of another embodiment of the present invention.

Referring now to FIG. 8, there is shown a device 80 as described above in combination with another device 82 as described above. These devices 80 and 82 are connected together by means of a pipe 84 that is connected between the outlet 16 of the device 80 and the inlet 14 of the other device 82. As it can be seen in this FIG. 8, several devices can be connected in series to increase purification of the flow of liquid.

Figure 9:
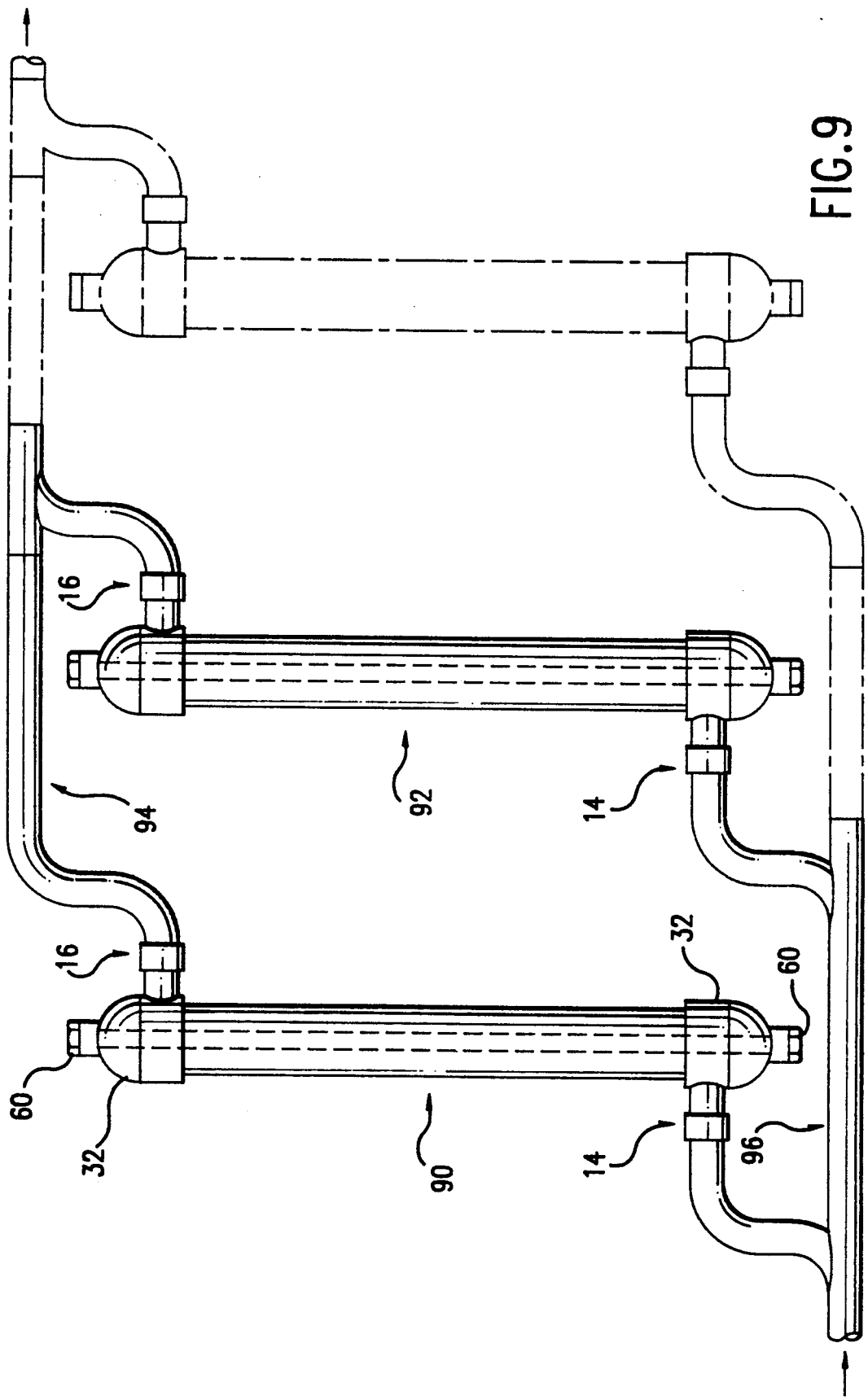
FIG. 9 is a side view of another embodiment of the present invention.

Referring now to FIG. 9, there is shown a device 90 as described above, in combination with another device 92 as described above. The devices 90, and 92 have their inlet 14 connected to first pipe network 94, and their outlet 16 connected to a second pipe network 96, whereby the flow of water can be treated faster. As it can be seen in this FIG. 9, several devices can be connected in parallel.

The outer casing 10 and the tubular elements 52 and 60 of the connector are made of opaque and water resistant material such as PVC. The present device can be installed in series immediately after conventional filtration systems, therefore greatly reducing the consumption of chemical products traditionally used for killing bacteria in swimming pools water. The provision of the inner casing 6 which is a protective transparent tube located between the ultraviolet lamp and the flow of water provides a protection for the ultraviolet lamp from the turbulent flow of water and also provides further safety by avoiding direct contact between the water and the ultraviolet lamp, therefore substantially reducing the risk of electrical fault.

Because of possible series and/or parallel connections between the devices, it can be easily sized for a specific range of flow rates in order to ensure effective use of ultraviolet rays to kill harmful bacteria in the water.

Because the present device can be made of PVC, it is designed to resist outside climatic conditions in order to be installed outside. Also, as the electrical supply box can be separated from the device, it can be installed adjacent to the device or at a remote location if required.

An air gap is present between the ultraviolet lamp 2 and the protective transparent tube 6. The drain valve 38 is necessary to empty the device from liquid when required.

Each end of the device has been designed for easy accessibility to the ultraviolet lamp 2 and the protective transparent tube 6. When assembling an end of the device, the end of the outer casing 10 which forms a female adaptor, is screwed on the first tubular element 52 which forms a male adaptor. Then, the seal 20 which forms a gasket is fitted tightly over the end of the protective transparent tube 6 therefore, sealing the flow passage 12 which forms a sterilization chamber. The washer 54 is then pressed against the gasket 50 by the male adaptor 52 which surrounds the electrical socket 22 feeding electricity to the ultraviolet lamp 2. The washer 66 which forms a gasket is mounted right against the male adaptor 52 and the electrical socket 22. The second tubular element 60 which forms an end female adaptor is then screwed on tightly to secure the gasket 66.

The length of the central portion 30 is determined by the length of the ultraviolet lamp 2 selected by the user. As a matter of fact, it will be appreciated that the majority of the parts of the present device are commercially available.

Figure 2:
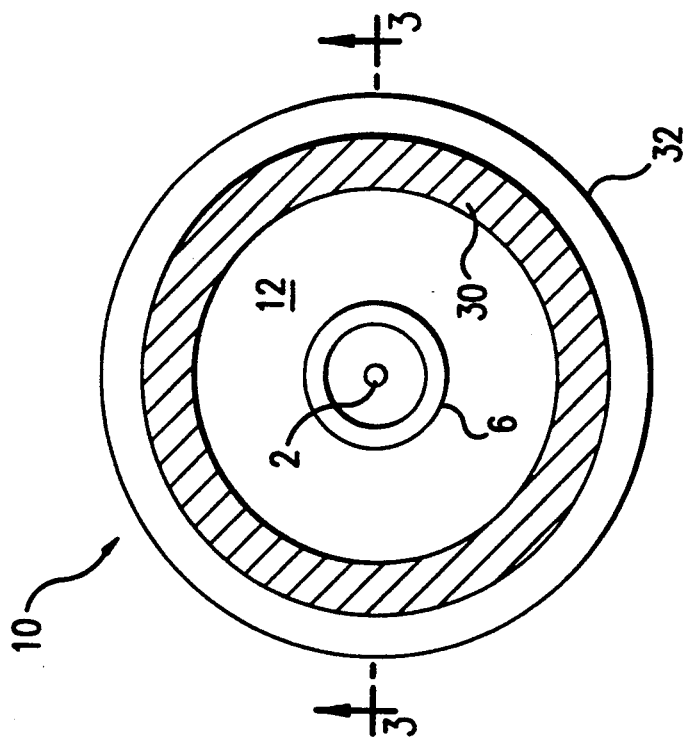
FIG. 2 is a cross-section view along line 2—2 of FIG. 1.
Figure 3:
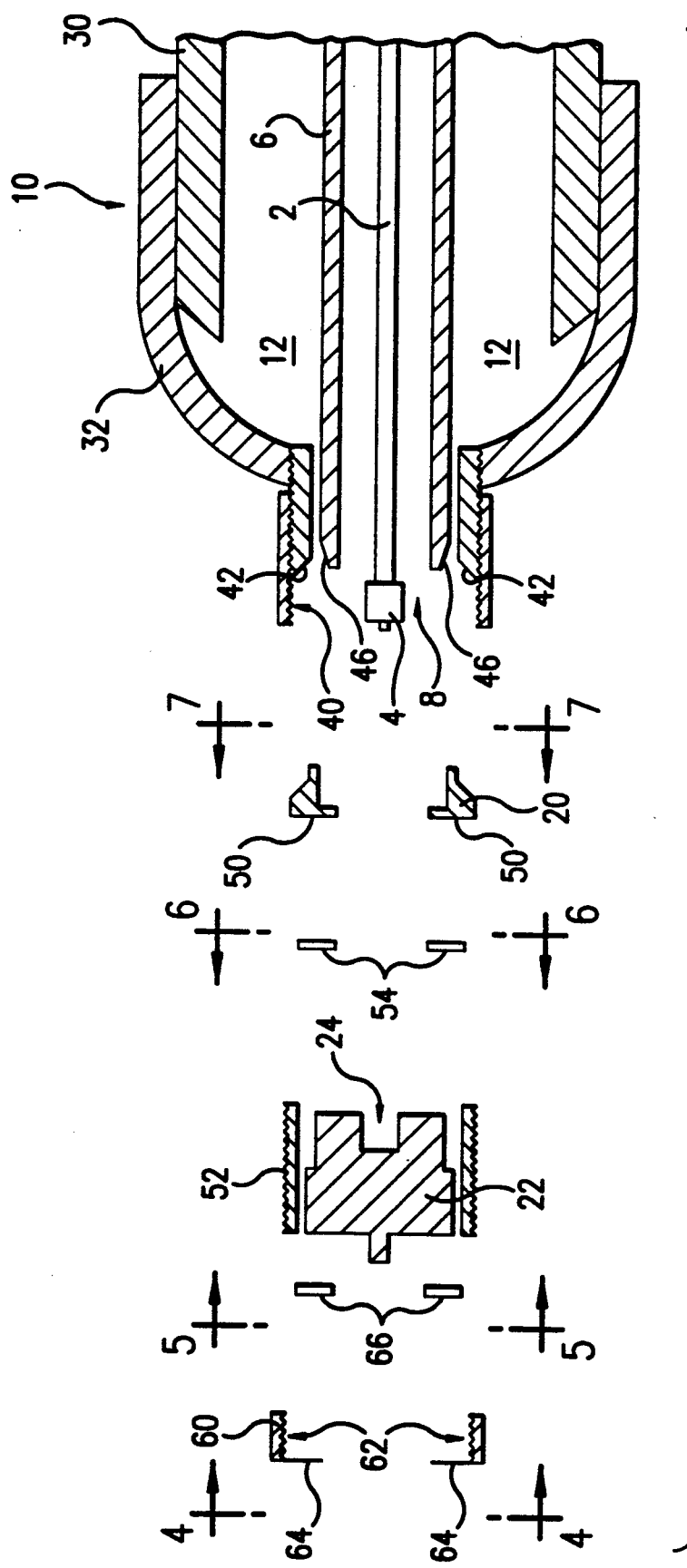
FIG. 3 is a cross-section view partially in an exploded view along line 3—3 of FIG. 2.
Figure 10:
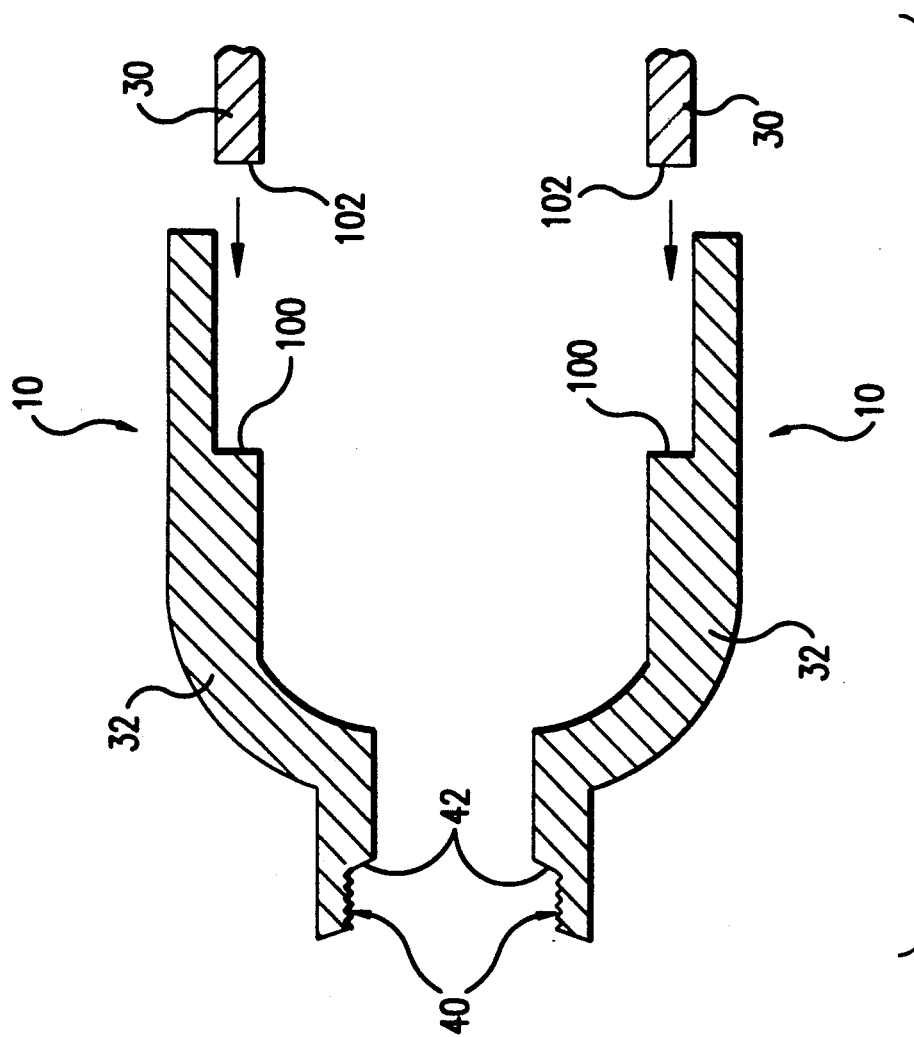
FIG. 10 is a cross-section view of end and central portions of the outer casing, along line 3—3 of FIG. 2.

Referring now to FIG. 10, there is shown in a cross-section view along 3—3 of FIG. 2, the outer casing 10 and the central portion 30. The embodiment shown in this FIG. 10 is specifically adapted for mass production when the outer casing 10 and the central portion 30 are made of opaque and water resistant material such as PVC. The outer casing 10 is provided with an inner stop 100 which is adapted to receive the end 102 of the central portion 30. After that the central portion 30 has been inserted inside the outer casing 10, they are stuck together by means of glue.

Preferably, all parts of the apparatus are made of water resistant material and are resistant to outside climatic conditions for operations above the water freezing point.

The use of a system including several devices according to the present invention, arrange in a combination of series and parallel connections with suitable valves and interconnecting pipes provide an extremely flexible system for varying circumstances. Furthermore, with such systems, one individual device may be shut off for tube replacement or other maintenance without interrupting the sterilization process.

Although the present invention has been explained hereinabove by way of a preferred embodiment thereof, it should be pointed out that any modifications to this preferred embodiment within the scope of the appended claims is not deemed to alter or change the nature and scope of the present invention.

I claim:

1. A device for purifying a flow of liquid by means of ultraviolet radiation, comprising:
   an elongated ultraviolet lamp having electrical terminals at each end thereof;
   a generally tubular inner casing surrounding substantially said lamp, said casing being made of a material that allows transmission of ultraviolet radiation, said casing having an aperture at each end thereof from which said electrical terminals protrude;
   a generally tubular outer casing surrounding said inner casing and forming with said inner casing a flow passage of generally annular cross-section for accommodating said flow of liquid, said outer casing being made of opaque material and wherein said outer casing comprises an elongated tubular central portion and two end portions disposed respectively at both sides of said central portion, each of said end portions having a first aperture for receiving the corresponding end of said central portion, each of said end portions being provided with a lateral aperture receiving a male barbed hose fitting forming an inlet or outlet, one of said end portions being provided with a drain valve, the other of said end portions being provided with a breather valve, each of said end portions being provided with a second aperture opposite to said first aperture to receive a corresponding connector, said second aperture being provided on its inner portion with threads and with a bevelled edge for receiving a corresponding annular seal;
   two connectors disposed respectively at both ends of said device for securing said lamp and said inner casing with respect to said outer casing, each of said connectors comprising:
   an opaque electrical socket having a central cavity for receiving the corresponding terminal of the lamp; and
   a fixing means for securing the corresponding socket and seal with respect to said casings and lamp; said casings, said seals and said sockets being made of material resistant to degradation by ultraviolet radiation.

2. A device according to claim 1, wherein:
   said inner casing has each of its ends provided with a bevelled edge for receiving the corresponding annular seal;
   each of said seals has an end provided with a protruding portion cooperating with the corresponding bevelled edges of said inner casing and end portions of said casing, and an opposite end provided with a stop;
   each of said fixing means comprises:
   a first tubular element having threads on its outer surface to be engaged with the threads of the corresponding end portion of said outer casing;
   an annular metal washer having one side to be disposed against said stop of the corresponding annular seal, and another side to receive an edge of the corresponding tubular element when it is screwed with the corresponding end portion of said outer casing to hold the corresponding annular seal in a liquid-tight position;
   a second tubular element having threads on its inner surface, to be engaged with the threads of the corresponding first tubular element, and provided with a stop at its outer end to rest against the corresponding first tubular element and socket when it is screwed upon the corresponding first tubular element; and
   an annular rubber washer to be disposed between said stop of the corresponding second tubular element and the corresponding first tubular element and socket.

3. A device according to claim 2, in combination with an electrical supply box having electrical wires to be connected respectively to said terminals of said lamp to energize said lamp.

4. A device according to claim 1, in combination with another device according to claim 1, further comprising a pipe connected between the outlet of one of said devices and the inlet of the other device, whereby said devices are connected in series.

5. A device according to claim 1, in combination with another device according to claim 1, further comprising a first pipe network connected to their inlet, and a second pipe network connected to their outlet.

6. A device according to claim 2, wherein said outer casing and said tubular elements are made of PVC.

* * * * *